United States Patent [19]

Silvey

[11] 4,342,221
[45] Aug. 3, 1982

[54] ENGINE CYLINDER HEAD PORT CLOSURE PAD CLAMP

[75] Inventor: Fred H. Silvey, Rowland Heights, Calif.

[73] Assignee: Irontite Products, Co. Inc., El Monte, Calif.

[21] Appl. No.: 173,224

[22] Filed: Jul. 28, 1980

[51] Int. Cl.³ .............................................. G01M 3/04
[52] U.S. Cl. .................................................... 73/49.7
[58] Field of Search ................... 73/49.7, 49.8; 138/90; 137/800

[56] References Cited

U.S. PATENT DOCUMENTS

| | | | |
|---|---|---|---|
| 2,897,669 | 8/1959 | Villers, Jr. et al. | 73/49.8 X |
| 3,360,984 | 1/1968 | Salsbury | 73/49.7 |
| 4,274,301 | 6/1981 | Katayama | 74/551.1 |

Primary Examiner—Jerry W. Myracle
Attorney, Agent, or Firm—Whann & McManigal

[57] ABSTRACT

A universal clamp for use in sealing the surface ports of an engine part possessing a fluid circulating jacket such as a cylinder head so that the part may be subjected to fluid pressure testing, which includes, a mounting member adapted to be positioned in an engine cylinder head bolt hole, consisting of an actuation element which extends through a fixed sleeve portion and is threadedly interconnected with a wedging sleeve portion for axial movement with respect to the fixed sleeve so as to engage the wedging and fixed portions and force them into wedging engagement with a portion of the wall of the bolt hole, thereby securing the clamp. Slotted arms are slidably and rotatably mounted on the mounting member so as to be radially adjustable to allow sealing of ports positioned at varying distances from the mounting member. Screw members threadedly interconnected with the arm members secure plug or other sealing structures thereby sealing the ports.

2 Claims, 3 Drawing Figures

ENGINE CYLINDER HEAD PORT CLOSURE PAD CLAMP

BACKGROUND OF THE INVENTION

Internal combustion engine cylinder heads and particularly diesel engine cylinder heads are complex castings possessing numerous internal coolant, fuel injector and exhaust gas passages. As pointed out in U.S. Pat. No. 3,973,429, Durgan, et al, in diesel engines higher pressures and temperatures are required for proper combustion of the fuel and under heavy service seals about the fuel injectors and pre-combustion chambers may leak. In addition, cracks may develop in the walls which separate the numerous internal passages which can cause a detrimental intermixing of coolant fluid, exhaust gases, fuel and lubricating oil.

The Durgan patent teaches that cylinder heads and the like can be tested for leaks by removing the engine head from the engine and sealing off the ports which connect the internal coolant passages with the corresponding passages in the engine block, and subjecting the cylinder head passages to compressed air or a fluid under pressure. By applying a soap or other suitable solution to the cylinder head or part to be tested, it is then possible to locate any cracks or leaks between the coolant passages and any other conduit.

A major problem in the pressure testing of cylinder heads is that the heads come in many different sizes and with numerous different configurations of coolant passages and parts thus requiring a variety of plates, plugs, pads and clamps to seal the part to be tested. A number of solutions to facilitate the sealing of a cylinder head for fluid pressure testing are disclosed in U.S. Pat. Nos. 3,360,984, Salsbury et al, 3,973,429, Durgan et al and 4,157,028, Moffett III. As disclosed in the above cited Patents, the parts may be sealed by means of various types of clamping structures. These prior art clamping structures all involve numerous pads, plates, bolts or springs and the clamping mechanisms tend to obstruct the engine head gasket mating surface interfering with access to the head surface for inspection and repair purposes. Also, these prior art clamps are often time consuming to adjust.

The present invention eliminates the shortcomings of the abovementioned prior art by providing an engine cylinder head port closure clamp for sealing the ports of engine cylinder heads or the like, which is of simpler design and is adaptable to virtually all models of cylinder heads. By virtue of being able to insert and secure the clamp in either a threaded or non-threaded cylinder head bolt hole of different diameters additional bolts, nuts or tie bars are eliminated permitting the sealing of the engine head ports to be more readily and rapidly accomplished. Also, the clamp of the present invention provides greater access to the cylinder head enabling greater use of inspection and faster more efficient repair of defects.

SUMMARY OF THE INVENTION

With the foregoing in mind, it is an object of the invention to provide a universal engine cylinder head port closure clamp to be used in fluid pressure testing of all types of engine cylinder heads which is of simple and economical design.

Another object is to provide a port closure clamp of the character described which includes means for rapidly positioning said clamp with respect to a cylinder head port closure pad.

Another object is to provide a port closure clamp which is secured to the part to be tested by a member being inserted into a cylinder head bolt hole.

Another object is to provide a closure clamp which enables the clamping of a plurality of port closure pads.

Still another object is to provide a universal port closure clamp adaptable to cylinder heads of various designs for securing port closure members.

Another object is to provide a port closure clamp that is adaptable to be secured in threaded or non-threaded cylinder head bolt holes of different diameters.

Another object is to provide a port closure clamp which allows maximum access to the cylinder head surface to facilitate inspection and repair.

Other objects and advantages of the invention will be made apparent in the course of the following description of preferred forms of the invention.

BRIEF DESCRIPTION OF THE DRAWINGS

Referring to the accompanying drawings.

DESCRIPTION OF THE PREFERRED EMBODIMENT

Figure 1:
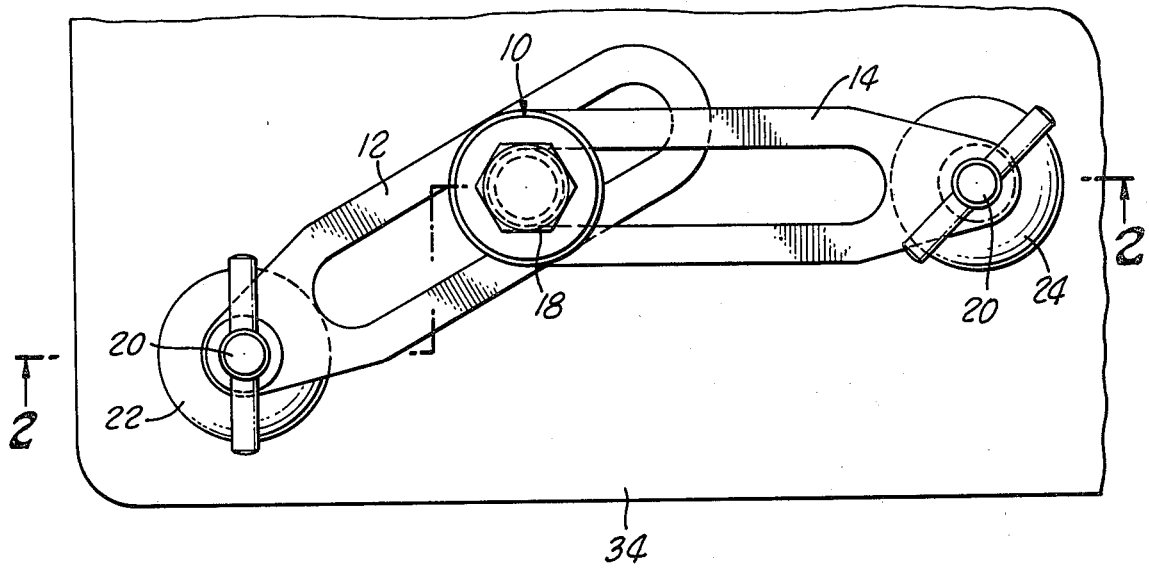
FIG. 1 is a plan view of the invention as installed on an engine cylinder head and securing two port closure pads.
Figure 2:
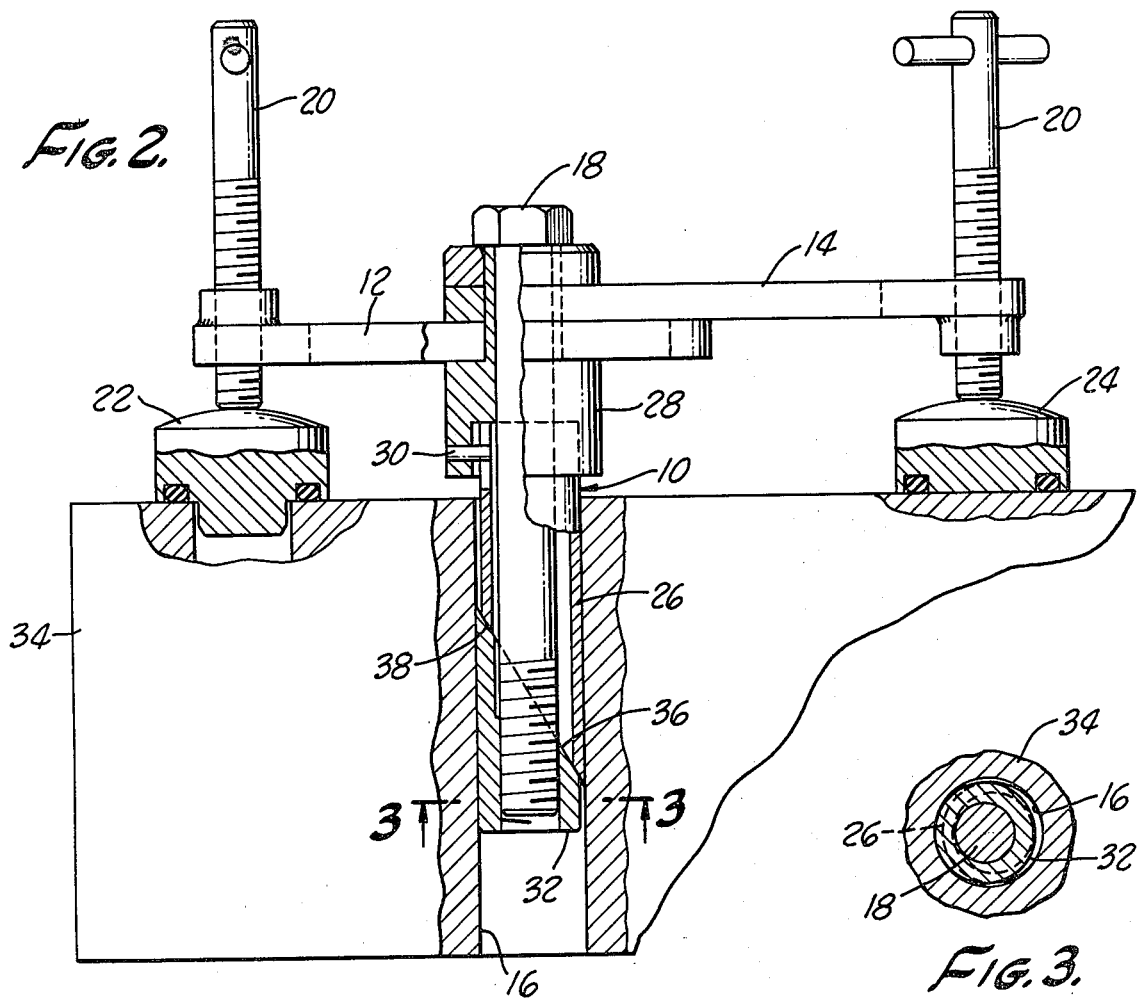
FIG. 2 is a cross sectional view taken along line 2—2 of FIG. 1.

Referring more specifically to the drawings, for illustrative purposes, the engine cylinder head port closure clamp of the present invention is disclosed in FIGS. 1 and 2, as comprising generally a cylindrical mounting member 10, adapted to be positioned in an engine cylinder head bolt hole 16; slotted, adjustable clamp arms 12 and 14 and manually operable screw members 20 whereby port closure members 22 and 24 are secured to the engine cylinder head gasket mating surface thereby sealing the ports so that the fluid circulating conduits may be subjected to a pressurized fluid for testing. More specifically, the cylindrical mounting member 10 includes a normally axially aligned fixed sleeve portion 26, which is secured to the collar portion 28 of the mounting member 10 by means of pin 30 and a cylindrical wedging portion 32 threadedly connected to actuation element 18.

Again referring to FIGS. 1 and 2, adjustable slotted arms 12 and 14 are slidably and rotatably mounted on collar 28 of mounting member 10 so that they may be positioned to seal ports at varying distances from the cylinder head bolt hole in which the clamp is secured. Manually operable screw members 20 are mounted at the ends of clamp arms 12 and 14 respectively, whereby port closure members 22 and 24 may be secured sealing the cylinder head ports.

In the alternative embodiments of the present inventions not illustrated by the drawings, a single clamp arm or three or more clamp arms may be incorporated into the present structure to accommodate cylinder heads with varying port configurations.

Figure 3:
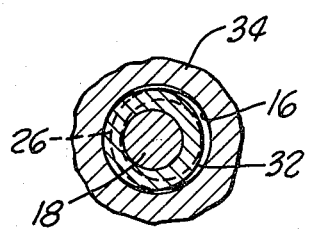
FIG. 3 is a fragmentary view taken along line 3—3 of FIG. 2, disclosing the clamp's mounting member engaging the walls of a cylinder head bolt hole.

To seal the ports of an engine cylinder head or the like utilizing the clamp of the present invention, the clamp is installed on the cylinder head 34 by inserting the cylindrical mounting member 10 into a cylinder head bolt hole 16. Actuation element or bolt 18 is then tightened, drawing the cylindrical wedging portion 32 of mounting member 10 upward such that the inclined surface 36 of wedging portion 32 comes into contact with the inclined surface 38 of the fixed sleeve portion 26. Further tightening of the actuation element 18 causes the wedging sleeve portion 32 to become laterally offset from the fixed sleeve portion 26 due to the diameter of the actuation element 18 being smaller than the bore of fixed sleeve portion 26, allowing lateral movement of actuation element 18. Thus upon insertion of the cylindrical mounting member 10 of the clamp assembly into a cylinder head bolt hole and the tightening of actuation element 18, the fixed sleeve portion 26 and the wedging sleeve portion 32 engage the walls of the bolt hole 16, as shown in FIG. 3 thereby securing the clamp assembly to the engine cylinder head 34.

Upon securing the clamp assembly to the cylinder head 34, the slotted clamp arms 12 and 14 are adjusted such that manually operable screw members 20 are positioned to bear on port closure members 22 and 24, whereupon tightening exerts a pressure on the respective port closure members 22 and 24, sealing the ports so that the cylinder head 34 can be tested by means of subjecting the water jacket and fuel conduits to a pressurized fluid.

Various modification may suggest themselves to those skilled in the art without departing from the spirit of my invention, and, hence, I do not wish to be restricted to the specific form shown or uses mentioned except to the extent indicated in the appended claims.

I claim:

1. A port closure clamp for use in sealing the surface ports of an engine part such as a cylinder head or the like possessing fluid circulating conduits, said clamp comprising:
   a. mounting means secured to said cylinder block having a mounting part positioned adjacent said mating surface of said cylinder block,
   b. an arm on said mounting part extending parallel to said mating surface,
   c. a port closure member on said arm,
   d. tightening means for tightening said closure member against said cylinder head to close a fluid circulating conduit of said cylinder head, and
   e. a longitudinal slot in said arm through which said mounting part extends whereby said arm may be radially movable with respect to said mounting part whereby the effective length of said arm may be shortened or lengthened.

2. A combination as defined in claim 1 in which there is a second arm extending radially from said mounting means, which arm has a cylinder head engaging element movable to engage said cylinder head to balance forces against said mounting part.

* * * * *